United States Patent

Schleigh et al.

[11] Patent Number: 5,183,894
[45] Date of Patent: Feb. 2, 1993

[54] 2-SUBSTITUTED-1-HYDROXYINDOLES

[75] Inventors: William R. Schleigh, Brockport; Thomas R. Welter, Webster, both of N.Y.

[73] Assignee: Eastman Kodak Company, Rochester, N.Y.

[21] Appl. No.: 724,232

[22] Filed: Jul. 1, 1991

Related U.S. Application Data

[63] Continuation-in-part of Ser. No. 562,997, Aug. 6, 1990, abandoned.

[51] Int. Cl.$^5$ .................. C07D 209/42; C07D 209/30; C07D 213/50; A01N 43/40
[52] U.S. Cl. .................................... 546/273; 548/466; 548/492; 548/493; 548/505; 548/506; 548/509; 548/511; 558/406
[58] Field of Search .............. 546/273; 548/466, 505, 548/492, 493, 509, 511, 506; 558/406

[56] References Cited

U.S. PATENT DOCUMENTS 3,296,277 1/1967 Petracek ..................... 260/326.16

FOREIGN PATENT DOCUMENTS 0151505 5/1979 Japan ........................... 548/505

OTHER PUBLICATIONS

Sword, J. Chem. Soc (C), 1970 pp. 1916-1922.
Bernard, et al., Chemical Abstracts, vol. 78, 1973, Abstract 43352u.
J. Agric. Food Chem., 23(4), 785 (1975) by Dekker, H. A. Selling and J. C. Overeem.
J. Chem. Soc., 3466 (1960) by Loudon and Tennant.
E. Fischer and H. Hutz, Chem. Ber., 28, 585 (1895).

Primary Examiner—Robert T. Bond
Assistant Examiner—E. C. Ward
Attorney, Agent, or Firm—Betty Joy Deaton

[57] ABSTRACT

The present invention relates to 2-substituted-1-hydroxyindoles of the following formula:

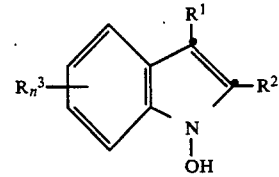

wherein,
  $R^1$ is an electron withdrawing group,
  $R^2$ is an alkenyl having 2–10 carbon atoms, and N-substituted α-iminobenzyl group wherein the substituents are selected from the group consisting of phenyl, anilino and dimethylamino, an unsubstituted aromatic group, and an aromatic group having meta or para substituents which are nitro, trifluoromethyl, fluoro, formyl, hydroxyiminomethyl and carbamoyl,
  $R^3$ is a halogen atom, and
  n is 0, 1, or 2, provided that when $R^2$ is either phenyl or nitro substituted phenyl and n is 0, then $R^1$ is not cyano.

10 Claims, No Drawings

2-SUBSTITUTED-1-HYDROXYINDOLES

RELATED APPLICATION

This application is a continuation-in-part of U.S. application Ser. No. 562,997 filed Aug. 6, 1990, now abandoned.

FIELD OF THE INVENTION

The present invention relates to compounds useful as fungicides.

BACKGROUND OF THE INVENTION

In view of world hunger, it is useful to provide the public with a variety of fungicides for use in food agriculture.

The general structure of 1-hydroxy-2-indoles is known in the art. Use of 1-hydroxy indoles as fungicides is not known in the art. Although a number of N-substituted indoles have been described as active fungicides, none listed as active fungicides had an oxygen substituent, as found in 1-hydroxy indoles.

U.S. Pat. No. 3,296,277 discloses 3-cyano-1-hydroxy-2-phenylindole in which the phenyl group at the 2-position of the indole nucleus bears a nitro lower alkoxy substituent at either the ortho, meta, or para position. These compounds are disclosed as having pharmacological activity, not as fungicides.

Loudon, et al., *Journal of the Chemical Society*, 3466 (1960) disclose the preparation of 3-cyano-1-hydroxy-2-phenylindole. Only phenyl, however, is discussed as a substituent in the 2-position of 1-hydroxyindole. Other substituents in the 2-position are not disclosed.

SUMMARY OF THE INVENTION

The present invention relates to novel 2-substituted-1-hydroxyindoles having the following formula:

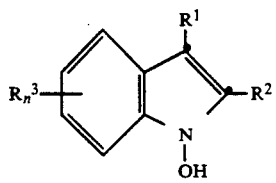

wherein, $R^1$ is an electron withdrawing group, $R^2$ is selected from the group consisting of alkenyl having 2-10 carbon atoms, an N-substituted α-iminobenzyl group wherein the substituents are selected from the group consisting of phenyl, anilino and dimethylamino, and an unsubstituted or substituted aromatic group having meta or para substituents selected from the group consisting of nitro, trifluoromethyl, fluoro, formyl, hydroxyiminomethyl and carbamoyl, $R^3$ is selected from the group consisting of halogen atoms, and n is 0, 1 or 2 provided that when $R^2$ is either phenyl or nitro substituted phenyl and n is 0, then $R^1$ is not cyano.

In one aspect of the invention, a 1-hydroxyindole is provided comprising the structure as shown above wherein $R^1$ is cyano, and $R^2$, $R^3$, and n are defined as above.

DETAILED DESCRIPTION OF THE PREFERRED EMBODIMENTS

The compounds of the present invention are useful in controlling foliar phytopathogenic fungi. The fungi are controlled by applying a fungicidally effective amount of one or more of the inventive compounds having the following formula:

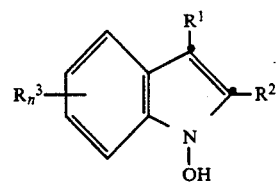

wherein, $R^1$ is an electron withdrawing group, such as carbamoyl, for example, carbamoyl, t-butylcarbamoyl, and dimethylcarbamoyl, carboxy, cyano and nitro;

$R^2$ is selected from the group consisting of alkenyl having 2-10 carbon atoms, such as vinyl, allyl or butenyl, an N-substituted α-iminobenzyl group wherein the substituents are attached to said imino group and are selected from the group consisting of phenyl, anilino and dimethylamino, such as α-(phenylimino)benzyl, α-(N'-phenylazino)benzyl and α-(N', N'-dimethylazino)benzyl, and an unsubstituted or substituted aromatic group having meta or para substituents selected from the group consisting of nitro, trifluoromethyl, fluoro, formyl, hydroxyiminomethyl and carbamoyl, such as phenyl, 4-nitrophenyl, 3-nitrophenyl, 3-trifluoromethylphenyl, 4-fluorophenyl, 4-formylphenyl, 4-carbamoylphenyl and 4-hydroxyiminomethylphenyl;

$R^3$ is a halogen atom, such as chloro, bromo, iodo or fluoro; and n is 0, 1 or 2.

In the compounds of this invention, when $R^2$ is either phenyl or nitro substituted phenyl and n is 0, then $R^1$ is not cyano.

Preferred compounds of the invention have the above structure wherein $R^1$ is cyano and $R^2$, $R^3$ and n are as described above.

Other preferred compounds of the invention have the above structure wherein, $R^1$ is cyano;

$R^2$ is 3-trifluoromethylphenyl, 4-fluorophenyl, 4-formylphenyl, 4-carbamoylphenyl, phenyl, 2-furyl, vinyl, 4-pyridyl, 2-pyridyl, α-(phenylimino)benzyl or hydroxyiminomethylphenyl; and n is 0 and represents no substituents at $R^3$.

Even more preferred compounds of the invention have the above structure wherein $R^1$ is cyano;

$R^2$ is phenyl, 4-nitrophenyl or methyl; and $R^3$ is chloro and n is 1 or 2 so that $R_n^3$ represents 5,6-dichloro or 6-chloro.

Even further preferred compounds of the invention have the above structure wherein $R^1$ is cyano;

$R^2$ is phenyl, 3-nitrophenyl, or 4-nitrophenyl;

$R^3$ is 6-chloro; and n is 1.

The most preferred compounds of the invention are compounds wherein $R^2$ is 3-nitrophenyl or 4-nitrophenyl.

Compounds representative of the present invention include:
3-cyano-1-hydroxy-2-(3-trifluoromethylphenyl)indole,
3-cyano-1-hydroxy-2-(4-fluorophenyl)indole,
3-cyano-1-hydroxy-2-(formylphenyl)indole,
3-cyano-1-hydroxy-2-(4-hydroxyiminomethylphenyl)indole,
3-cyano-6-chloro-1-hydroxy-2-(4-nitrophenyl)indole,
3-cyano-5,6-dichloro-1-hydroxy-2-phenylindole,
3-cyano-6-chloro-1-hydroxy-2-phenylindole,
3-cyano-2-(2-furyl)-1-hydroxyindole,
3-cyano-1-hydroxy-2-vinylindole,
3-cyano-1-hydroxy-2-(4-pyridyl)indole,
3-cyano-1-hydroxy-2-(2-pyridyl)indole,
3-cyano-2-(3,4-dimethoxybenzoyl)-1-hydroxyindole,
3-cyano-1-hydroxy-2-[α-(phenylimino)benzyl]indole,
3-cyano-1-hydroxy-2-[α-(phenylazino)benzyl]indole and
3-cyano-2-[α-(dimethylazino)benzyl]-1-hydroxyindole.

The 2-substituted 1-hydroxyindoles are generally obtainable as colorless to yellow crystalline materials having characteristic melting points and absorption spectra and which may be purified by recrystallization from common organic solvents. They are appreciably soluble in many organic solvents such as methanol, ethanol, acetone, chloroform, benzene, dioxane, dimethyl sulfoxide and N,N-dimethylformamide, but are relatively insoluble in water.

The compounds of the invention can be prepared in general through minor modifications of literature procedures.

The synthesis of 1-hydroxy-3-cyano-2-phenylindole was first described by Loudon and Tennant in *J. Chem. Soc.*, 3466(1960). This preparation is represented by the following reaction scheme:

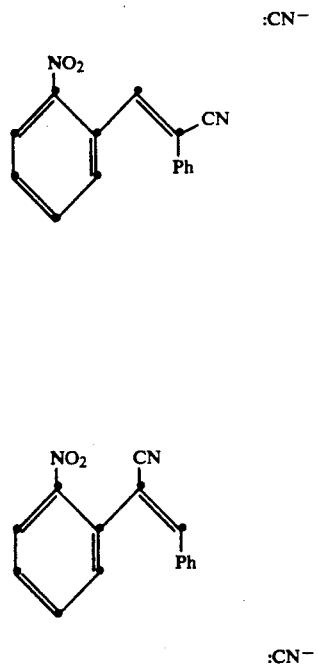

The preparation involved the cyanide induced cyclization of either of two 2-nitrophenyl-substituted cyanostilbenes.

Further development towards the preparation of 1-hydroxyindoles is seen in the work of F. J. Petracek shown in U.S. Pat. No. 3,296,277 which discloses the preparation of indoles containing substituted phenyls in the 2-position as seen in the following reaction scheme:

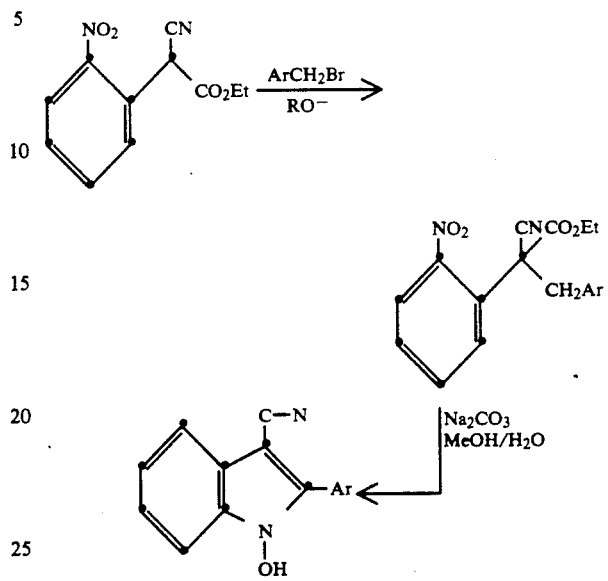

This synthesis involves the condensation of ethyl 2-nitrophenylcyano acetate with various benzyl halides under basic conditions followed by aqueous alkaline rearrangement providing 2-aryl-3-cyano-1-hydroxyindoles. The free hydroxyl group is preferred for activity. Other compounds can be prepared by the acid rearrangement of the well known benzoin oximes through the method described by E. Fischer in *Chemische Berichte*, 28,585 (1895).

The compounds of the invention can be prepared by using a slight modification of the method of Petracek as discussed hereinabove in reference to U.S. Pat. No. 3,296,277. 2-Halonitrobenzene can be condensed with ethyl cyanoacetate in the presence of excess potassium hydroxide affording a good yield of the ethyl 2-cyano-2-nitrophenylacetate as can be seen by the following reaction scheme:

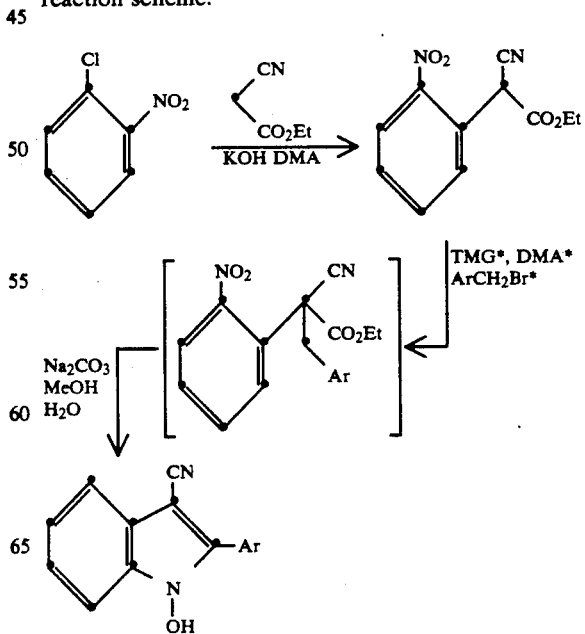

*ArCH₂X where X is halo preferably chloro or bromo
*TMG = 1,1,3,3,-tetramethylguanidine
*DMA = N,N-dimethylacetamide Various benzyl halides can then be condensed with the acetate ester followed by cyclization to the aryl-substituted indole as shown. Bromides are preferred.

The compounds of the invention were particularly tested for activity against *Colletotrichum lagenarium* (Anthracnose on cucumbers), *Puccinia recondita* (wheat leaf rust), *Erisiphe polygoni* (powdery mildew on beans), *Phytophthora infestans* (late blight on tomatoes), *Rhizoctonia solani* (Rhizoctonia on cotton), *Pythium sp.* (damping off on peas) and *Botrytis Cinerea* (gray mold). They showed particularly enhanced activity against rust disease, including *Puccinia recondita* (wheat leaf rust).

The introduction of highly hydrophilic groups such as carboxylate or sulfamoyl was found to decrease activity. Further, the introduction of highly hydrophobic groups such as 4-phenylsulfonylphenyl, benzophenonyl, t-butylphenyl were also found to decrease activity.

Preparation of Ethyl Cyano-2-nitrophenyl-acetate

A mixture of 2-chloronitrobenzene (47.2 g, 0.300 mole) and ethyl cyanoacetate (40 ml, 0.38 mol) in N,N-dimethylacetamide (DMA, 250 ml) was treated at once with potassium hydroxide pellets (120 g, 2.14 mole). The mixture was mechanically stirred and heated for ten minutes at 110°-120° C. (caution: minimal heat application may be needed, exothermic reaction) then poured into ice-cold dilute hydrochloric acid. Ether extractive workup gave an oil. The oil was passed through silica gel eluting with toluene to provide a yellow oil, which was dissolved in 100 ml methanol then chilled. The solid was filtered to afford ethyl cyano-2-nitrophenylacetate as a yellow solid (51.4 g, 73.2%) mp 57°-61° C. (literature 59°-60° C.).

EXAMPLE 1

Preparation of 1-Hydroxy-3-cyano-2-(4-trifluoromethylphenyl)indole

A mixture of ethyl cyano-2-nitrophenylacetate (4.68 g, 20.0 mmole), 4-trifluoromethylbenzyl bromide (4.77 g, 20.0 mmole), 1,1,3,3-tetramethylguanidine (TMG, 2.81 ml, 22.4 mmole) in DMA (50 ml) was heated to 100° C. Two additional 0.2 ml portions of the benzyl bromide were added at 15 min intervals. After a final 15 min the mixture was poured into water. Ethyl acetate extractive workup afforded the alkylated product as an oil. This oil in methanol (80 ml) with aqueous sodium carbonate (20 ml, 1.0M) was heated at reflux for 5 h then poured into ice-cold dilute hydrochloric acid. The solid was filtered, air dried then recrystallized twice from toluene to afford N-hydroxy-3-cyano-2-(4-trifluoromethylphenyl)indole as a cream solid (3.81 g, 63.1%) mp 202°-203° C. (at which temperature it decomposed).

EXAMPLES 2 to 11

The compounds described in the following Tables I and II, which also contain the melting points and elemental analyses for these compounds, were prepared by the procedure of Example 1 and the hereinabove described modified procedures of Petracek, except using the appropriate starting materials in equivalent amounts.

TABLE I

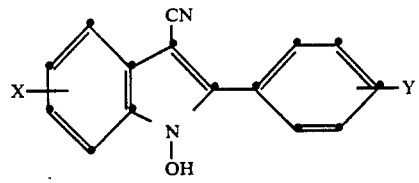

| Example | X | Y | mp(°C.)[a] | N | C | H |
|---|---|---|---|---|---|---|
| 3 | H | 3-CF₃ | 187–188 | 9.2 | 63.6 | 3.0 |
| | | | | 9.3 | 63.6 | 3.0 |
| 4 | H | 4-F | 208–209 | 10.5[b] | 72.4 | 3.9 |
| | | | | 10.7 | 72.1 | 3.8 |
| 5 | H | 4-CHO | 207–209 | 11.1[c] | 72.5 | 4.0 |
| | | | | 11.8 | 72.5 | 4.0 |
| 6 | H | 4-CH=NOH | 200–205 | 15.6 | 68.9 | 4.1 |
| | | | | 15.2 | 69.3 | 4.0 |
| 7 | 6-Cl | 4-NO₂ | 252 | 13.2[d] | 56.7 | 2.6 |
| | | | | 13.2 | 56.6 | 2.3 |
| 8 | 5,6-Cl₂ | H | 223–224 | 10.0[e] | 59.3 | 2.9 |
| | | | | 10.1 | 59.4 | 2.8 |
| 9 | 6-Cl | H | 225–227 | 10.5 | 67.1 | 3.5 |
| | | | | 10.4 | 67.0 | 3.4 |

(% Found) / (% Calculated) for Elemental Analysis columns N, C, H.

TABLE II

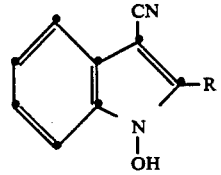

| Example | R | mp(°C.)[a] | N | C | H |
|---|---|---|---|---|---|
| 10 | —CH=CH₂ | 182–183 | 14.9 | 71.4 | 4.5 |
| | | | 15.2 | 71.7 | 4.4 |
| 11 | (furyl) | 219–220 | 12.8[f] | 69.0 | 3.8 |
| | | | 12.9 | 69.4 | 3.7 |

Key to Table I and II footnotes:
[a] All compounds melted with decomposition.
[b] through [f] Although all samples were dried in vacuo, certain samples retained solvent of crystallization. Therefore, the calculated values of the elements (N, C and H) for certain examples were based on retentions of specific molar ratios of solvent as follows:

| Footnote | Example | Solvent | Molar Ratio of Compound/Solvent |
|---|---|---|---|
| b | 4 | Toluene | 15/2 |
| c | 5 | Acetonitrile | 3/1 |
| d | 7 | Water | 4/1 |
| e | 8 | Acetonitrile | 4/1 |
| f | 11 | Acetonitrile | 10/1 |

EXAMPLE 12

Preparation of
3-cyano-1-hydroxy-2-[α-(phenylimino)-benzyl]indole

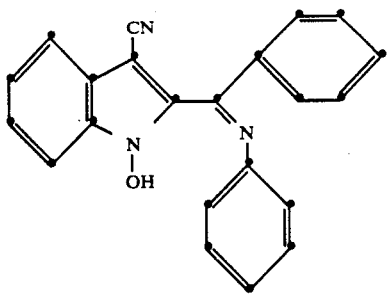

A mixture of 3-cyano-2-benzoyl-1-hydroxy-indole (2.62 g, 10.0 mmole) and aniline (1.0 g, 10.8 mmole) were heated at reflux in toluene (50 ml) under a trap for 16 hours. Concentration in vacuo afforded a solid. Recrystallization from methylcyclohexane provided dark crystals, m.p. 188°-190° C. Analysis (dry 25° C.): Fd(calculated) N, 12.2 (12.4), C, 78.2 (78.3) H, 4.7 (4.5).

EXAMPLE 13

Preparation of
3-cyano-1-hydroxy-2-[α-(phenylazino)-benzyl]]indole

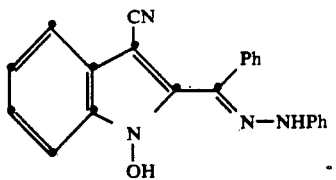

A mixture of 3-cyano-2-benzoyl-1-hydroxy-indole (2.62, 10.0 mmole) and phenylhydrazine (1.1 ml, 11.1 mmole) was heated at reflux in ethanol (35 ml) for fifteen minutes. The mixture was treated with additional phenylhydrazine (0.25 ml, 2.5 mmole) and stirred at ambient temperature for 16 hours. The mixture was concentrated in vacuo then triturated with ether-ligroin mixture to give a yellow solid. Recrystallization from acetic acid yielded a bright yellow solid which was dried in vacuo at 80° C., mp 154°-158° C. Analysis (dry 25° C.): Fd(calculated 12.5 mole % acetic acid) N, 15.7 (15.5), C, 74.2 (74.2), H, 4.6 (4.7).

EXAMPLE 14

Preparation of
3-cyano-2-[α-(dimethylazino)benzyl]-1-hydroxyindole.

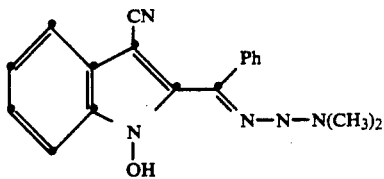

This compound was prepared as described for Example 13. A yellow solid, mp 164°-165° C., was obtained. Analysis (dry 25° C.): Fd (Calculated 11 mole % methanol) N, 18.2 (18.2), C, 70.5 (70.6), H, 5.3 (5.4).

The invention has been described in detail with particular reference to preferred embodiments thereof, but it will be understood that variations and modifications can be effected within the spirit and scope of the invention.

What is claimed is:

1. A compound having the following formula:

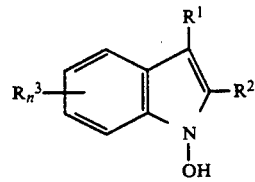

wherein, $R^1$ is carbamoyl, t-butylcarbamoyl, dimethylcarbamoyl, carboxy, nitro or cyano;

$R^2$ is an alkenyl having 2–10 carbon atoms, and an N-substituted α-iminobenzyl group wherein the substituents are selected from the group consisting of phenyl, anilino and dimethylamino, or an aromatic group selected from the group consisting of phenyl, 4-nitrophenyl, 3-nitrophenyl, 3-trifluoromethylphenyl, 4-fluorophenyl, 4-formylphenyl, 4-carbamoylphenyl and 4-hydroxyiminomethylphenyl;

$R^3$ is a halogen atom; and n is 0,1 or 2 provided that when $R^2$ is either phenyl or nitro substituted phenyl and n is 0, then $R^1$ is not cyano.

2. The compound of claim 1 wherein $R^1$ is cyano.

3. The compound of claim 1 wherein $R^1$ is cyano, $R^2$ is phenyl, 4-nitrophenyl, 3-nitrophenyl or methyl;

$R^3$ is chloro and n is 1 or 2.

4. The compound of claim 3 wherein $R^3$ is 6-chloro and n is 1.

5. The compound of claim 4 wherein $R^2$ is 4-nitrophenyl.

6. The compound of claim 4 wherein $R^2$ is 3-nitrophenyl.

7. The compound of claim 1 selected from the group consisting of:

3-cyano-1-hydroxy-2-(3-trifluoromethylphenyl) indole,
3-cyano-1-hydroxy-2-(4-fluorophenyl) indole,
3-cyano-1-hydroxy-2-(formylphenyl) indole,
3-cyano-1-hydroxy-2-(4-hydroxyiminomethylphenyl) indole,
3-cyano-6-chloro-1-hydroxy-2-(4-nitrophenyl) indole,
3-cyano-5,6-dichloro-1-hydroxy-2-phenylindole,
3-cyano-6-chloro-1-hydroxy-2-phenylindole,
3-cyano-2-(3,4-dimethoxybenzoyl)-1-hydroxyindole,
3-cyano-1-hydroxy-2-[α-(phenylimino)benzyl]indole,
3-cyano-1-hydroxy-2-[α-(phenylazino)benzyl]indole, and
3-cyano-2-[α-(dimethylazino)benzyl]-1-hydroxyindole.

8. The compound of claim 7 is 3-cyano-6-chloro-1-hydroxy-2-(4-nitrophenyl) indole or 3-cyano-6-chloro-1-hydroxy-2-phenylindole.

9. A compound having the following formula:

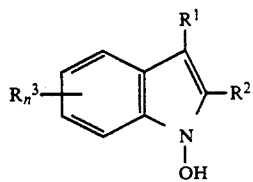

wherein,

R¹ is cyano,

R² is 3-trifluoromethylphenyl, 4-methoxyphenyl, 4-fluorophenyl, 4-formylphenyl, 4-carbamoylphenyl, 2-furyl, vinyl, 4-pyridyl, 2-pyridyl and α-(phenylimino)benzyl; and n is 0.

10. A compound having the following formula:

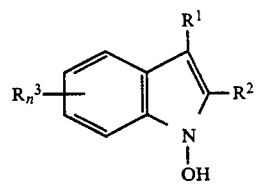

wherein,

R¹ is carbamoyl, t-butylcarbamoyl, dimethylcarbamoyl, carboxy, nitro or cyano;

R² is an alkenyl having 2–10 carbon atoms, and an N-substituted α-iminobenzyl group wherein the substituents are selected from the group consisting of phenyl, anilino and dimethylamino, or an aromatic group selected from the group consisting of phenyl, 4-nitrophenyl, 3-nitrophenyl, 3-trifluoromethylphenyl, 4-fluorophenyl, 4-formylphenyl, 4-carbamoylphenyl and 4-hydroxyiminomethylphenyl;

R³ is a halogen atom; and n is 0, 1 or 2 provided that when R² is either phenyl or nitro substituted phenyl and n is 0, then R¹ is not cyano.

* * * * *